(12) United States Patent
Nagai et al.

(10) Patent No.: US 7,981,384 B2
(45) Date of Patent: Jul. 19, 2011

(54) LIQUID ASPIRATOR AND ANALYZER PROVIDED WITH SAME

(75) Inventors: Takaaki Nagai, Kobe (JP); Noriyoshi Yoshida, Kobe (JP)

(73) Assignee: Sysmex Corporation, Kobe-shi (JP)

( * ) Notice: Subject to any disclaimer, the term of this patent is extended or adjusted under 35 U.S.C. 154(b) by 1186 days.

(21) Appl. No.: 10/890,879

(22) Filed: Jul. 14, 2004

(65) Prior Publication Data

US 2005/0013744 A1 Jan. 20, 2005

(30) Foreign Application Priority Data

Jul. 15, 2003 (JP) ................................. 2003-197379

(51) Int. Cl.
*B01L 3/02* (2006.01)
*G01N 1/14* (2006.01)
*G01N 35/10* (2006.01)

(52) U.S. Cl. ..................... 422/509; 422/501; 73/863.01; 73/864.11; 73/864.24; 436/180

(58) Field of Classification Search ......................... None
See application file for complete search history.

(56) References Cited

U.S. PATENT DOCUMENTS

| | | | | |
|---|---|---|---|---|
| 4,325,909 A * | 4/1982 | Coulter et al. | ................... | 422/63 |
| 5,141,871 A * | 8/1992 | Kureshy et al. | ................ | 436/47 |
| 5,455,008 A * | 10/1995 | Earley et al. | ............... | 73/864.24 |
| 5,895,630 A * | 4/1999 | Skaborn et al. | ............... | 422/100 |
| 6,171,280 B1 | 1/2001 | Imazu et al. | | |
| 6,234,033 B1 * | 5/2001 | Eipel | ........................... | 73/864.25 |
| 6,270,726 B1 * | 8/2001 | Tyberg et al. | ................. | 422/100 |
| 6,363,802 B1 * | 4/2002 | Grippo et al. | ............... | 73/864.24 |
| 7,284,453 B2 * | 10/2007 | Li et al. | ........................ | 73/863.01 |
| 2001/0012973 A1 * | 8/2001 | Wehrli et al. | .................. | 700/193 |
| 2002/0064481 A1 * | 5/2002 | Ishizawa et al. | ................. | 422/64 |
| 2007/0012123 A1 * | 1/2007 | Li et al. | ....................... | 73/863.01 |

FOREIGN PATENT DOCUMENTS

| | | |
|---|---|---|
| EP | 452892 A2 | 10/1991 |
| EP | 984285 A2 | 3/2000 |
| EP | 1291659 A2 | 3/2003 |
| GB | 2068115 A | 8/1981 |
| JP | 64-59158 | 3/1989 |
| JP | 64-059158 | 3/1989 |
| JP | 11-271322 | 10/1999 |
| JP | 11-304819 | 11/1999 |
| JP | 11-352132 | 12/1999 |
| JP | 2000-074927 | 3/2000 |
| JP | 2000-074928 | 3/2000 |
| JP | 2000-088862 | 3/2000 |
| JP | 2002-228670 | 8/2002 |
| WO | WO 00/58736 | 10/2000 |

OTHER PUBLICATIONS

European Search Report for European Application No. 08006055, dated Aug. 19, 2009, 3 pages.

\* cited by examiner

*Primary Examiner* — P. Kathryn Wright
(74) *Attorney, Agent, or Firm* — Brinks Hofer Gilson & Lione

(57) ABSTRACT

Liquid aspirators are described that include an aspirating pipette; a drive source for descending the aspirating pipette; and a controller for controlling the drive source; the aspirating pipette being stopped from being descended by loss of synchronism of the drive source caused by upward force to be exerted on the aspirating pipette.
Analyzers are also described.

6 Claims, 8 Drawing Sheets

U.S. 7,981,384 B2

LIQUID ASPIRATOR AND ANALYZER PROVIDED WITH SAME

RELATED APPLICATIONS

This application claims priority under 35 U.S.C. §119 to Japanese Patent Application No. 2003-197379, filed Jul. 15, 2003.

FIELD OF THE INVENTION

The present invention relates to a liquid aspirator and an analyzer provided with the same and, more particularly, to a liquid aspirator, in which liquid can be aspirated from a container containing therein liquid in a fine quantity.

BACKGROUND

The following have been known as techniques relating to the present invention:

(1) a liquid aspirator comprising a motor for inserting an aspirating pipette into a liquid container so as to press the tip of the aspirating pipette against the bottom of the container, and detecting means for detecting the pressed state, wherein the detecting means includes a liquid container support table urged by a spring and an optical detector or an electromotive detector of the motor, thereby securing the contact of the tip of the aspirating pipette with the bottom of the liquid container (disclosed in, for example, Int'l Pat. Appln. Publication No. 00/58,736); and (2) a liquid aspirator configured such that when liquid contained in a container for containing the liquid therein is aspirated by the use of an elevatable aspiration nozzle by descending the aspiration nozzle down to the bottom of the container in an elastically abuttable manner, the aspiration nozzle is descended at a predetermined descending speed from its top dead center down to a descendant level which has been previously set such that the tip of the nozzle is brought into contact with the bottom of the container with a high possibility, and thereafter, the aspiration nozzle is descended at a speed lower than the predetermined descending speed (disclosed in, for example, Jpn. Pat. Appln. KOKAI Publication No. 271,322/1999).

However, the above-described conventional devices have required a mechanical mechanism for bringing the aspirating pipette and the liquid container into an elastic contact with each other or an optical or electric detecting mechanism for detecting the contact condition, thereby raising a problem of a complicated configuration.

SUMMARY

The scope of the present invention is defined solely by the appended claims, and is not affected to any degree by the statements within this summary.

First liquid aspirator embodying feature of the present invention can aspirate liquid in a fine quantity contained in a liquid container by securing the contact of the tip of an aspirating pipette with the bottom of the container with a remarkably simple configuration.

Second liquid aspirator embodying feature of the present invention includes an aspirating pipette; a drive source for descending the aspirating pipette; and a controller for controlling the drive source; the aspirating pipette being stopped from being descended by loss of synchronism of the drive source caused by upward force to be exerted on the aspirating pipette.

Third liquid aspirator embodying feature of the present invention includes an aspirating pipette; a motor for descending the aspirating pipette; a motor drive unit for supplying a motor drive current to the motor; and a controller for controlling the motor drive unit in such a manner that the motor drive current to be supplied to the motor by the motor drive unit becomes small until the aspirating pipette is brought into contact with the bottom of the liquid container disposed under the aspirating pipette after the start of the descendent movement of the aspirating pipette.

Fourth liquid aspirator embodying feature of the present invention includes an aspirating pipette; a drive source for descending the aspirating pipette; and a controller for instructing the drive source to descend the aspirating pipette by a distance greater than a distance between the bottom of the liquid container disposed under the aspirating pipette and the tip of the aspirating pipette; the aspirating pipette descending according to the drive of the drive source while being stopped from being descended with the application of reactive force from the liquid container in contact with the bottom of the liquid container.

Fifth liquid aspirator embodying feature of the present invention includes an aspirating pipette; a drive source for descending the aspirating pipette; and a controller for controlling the drive source in such a manner as to descend the aspirating pipette so as to bring the aspirating pipette into contact with the bottom of the liquid container disposed under the aspirating pipette; the synchronization of the drive source being lost by bringing the aspirating pipette into contact with the bottom of the liquid container.

First Analyzer embodying feature of the present invention can be operated in a first mode in which liquid is aspirated from an open container through a first aspirating pipette for aspirating the liquid from the open container and in a second mode in which liquid is aspirated from a closed container through a second aspirating pipette for aspirating the liquid from the closed container.

Second analyzer embodying feature of the present invention includes an aspirating pipette holding member capable of selectively holding the first aspirating pipette and the second aspirating pipette; a drive source for descending the aspirating pipette holding member; and a controller for varying a descending process of the aspirating pipette holding member between the first mode and the second mode.

DETAILED DESCRIPTION OF THE EMBODIMENT

Blood Analyzer

Figure 1:
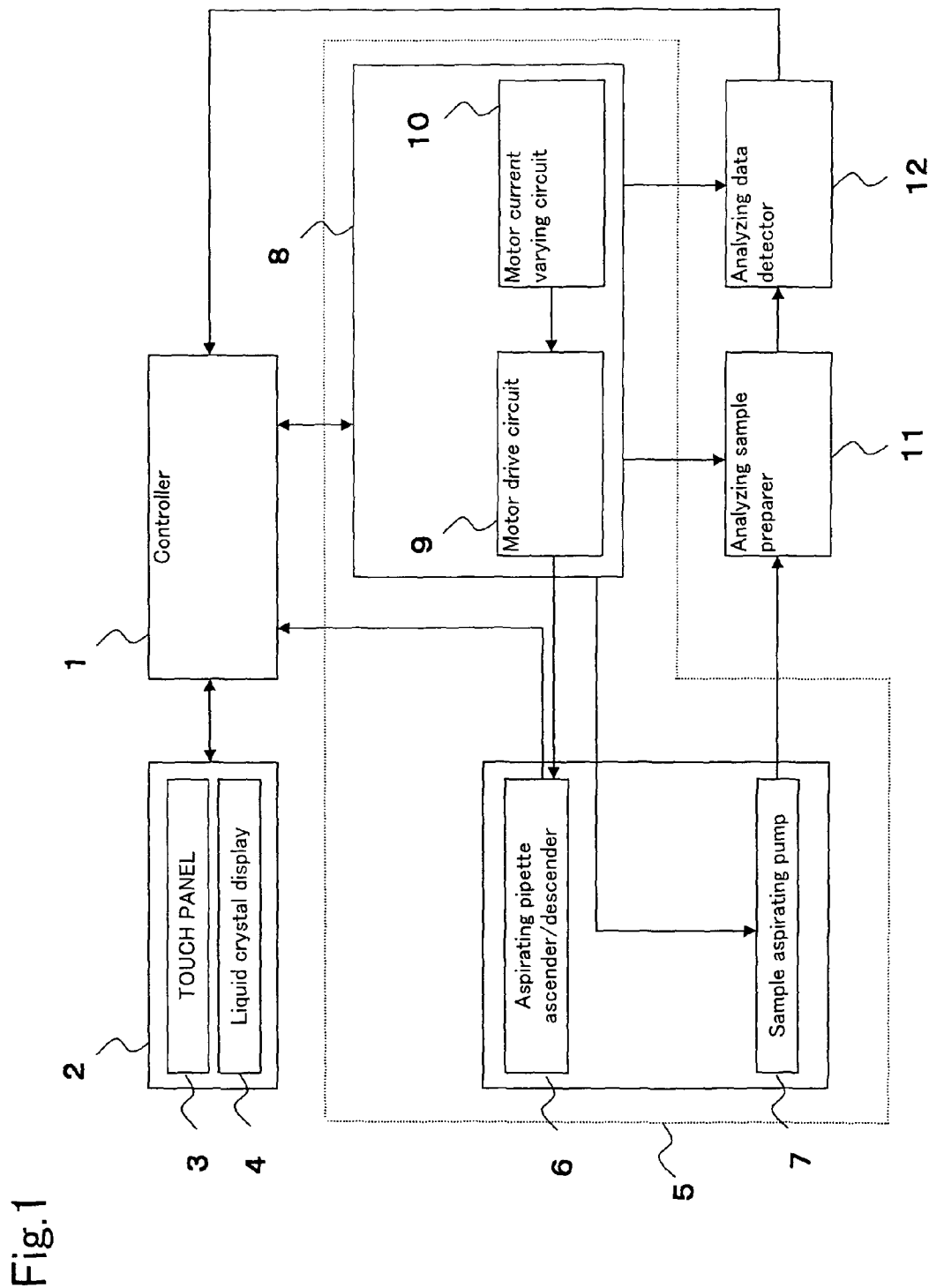
FIG. 1 is a block diagram illustrating a blood analyzer in a preferred embodiment according to the present invention.

FIG. 1 is a block diagram illustrating the configuration of a blood analyzer in a preferred embodiment according to the present invention. In FIG. 1, a controller 1 includes a CPU, a ROM, a RAM, an I/O port and the like. The controller 1 actuates a drive circuit unit 8 upon receipt of outputs from a touch panel 3 in an input/output unit 2 and an aspirating pipette ascender/descender 6 in a liquid aspirator 5. The liquid aspirator 5 includes the aspirating pipette ascender/descender 6, a sample aspirating pump 7 and the drive circuit unit 8.

The drive circuit unit 8 is adapted to drive the aspirating pipette ascender/descender 6, the sample aspirating pump 7, an analyzing sample preparer 11 and an analyzing data detector 12. The controller 1 performs an analysis upon receipt of detection data from the analyzing data detector 12, and then, outputs the analysis result to a liquid crystal display 4 in the input/output unit 2.

Aspirating Pipette Ascender/Descender

Figure 2:
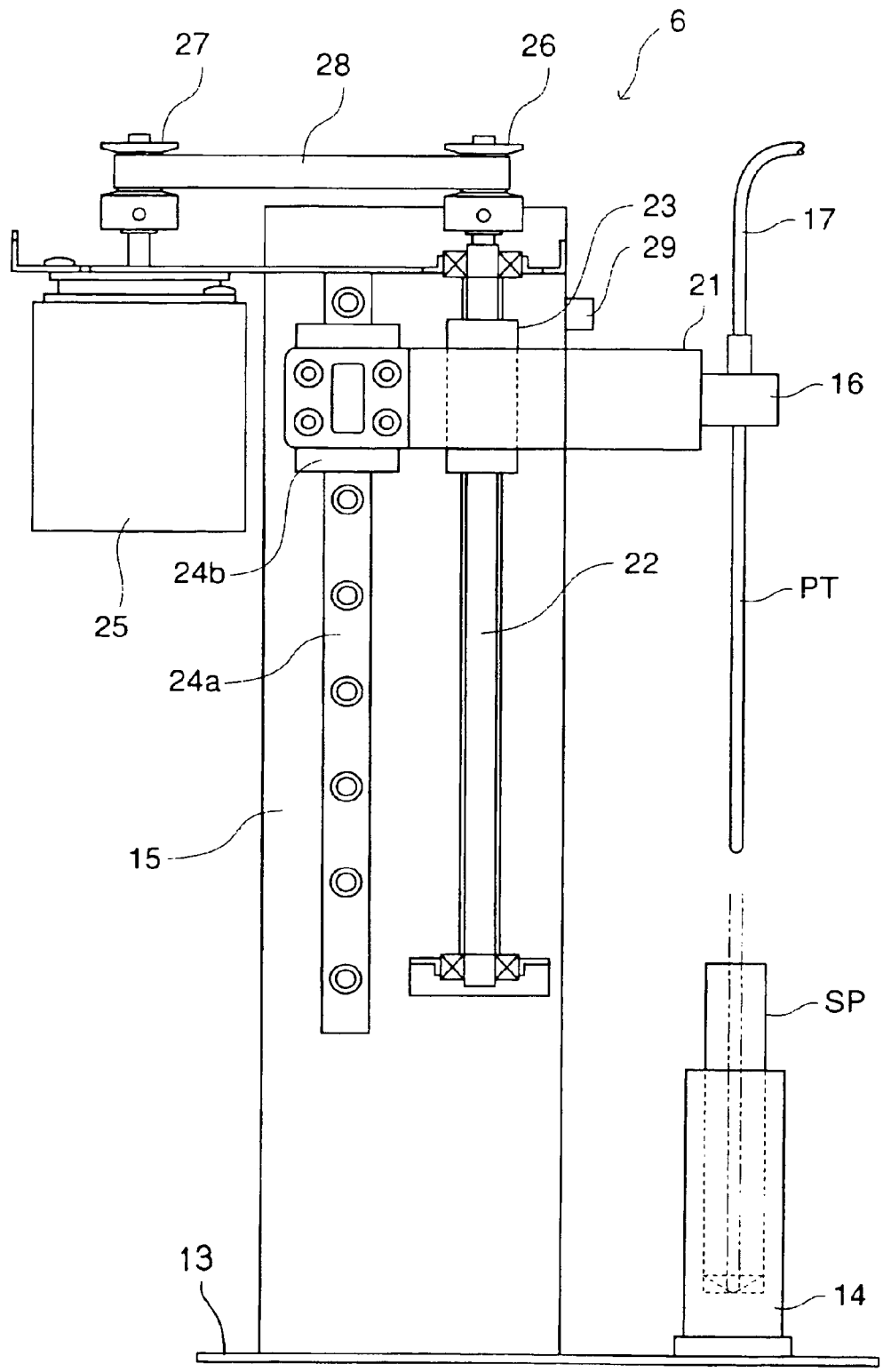
FIG. 2 is a front view showing essential parts of the blood analyzer illustrated in FIG. 1.

FIG. 2 is a front view showing the aspirating pipette ascender/descender 6.

As shown in FIG. 2, the aspirating pipette ascender/descender 6 includes a base table 13, a support plate 15 erected on the base table 13, an elongated horizontal arm 21 extending in a horizontal direction with respect to the support plate 15, a screw shaft 22 penetrating the horizontal arm 21 in a vertical direction and being rotatably supported by the support plate 15, a nut 23 engaging with the screw shaft 22 via a screw and being fixed to the horizontal arm 21, a slide rail 24a disposed in the support plate 15 in parallel to the screw shaft 22, a sliding member 24b disposed at the left end of the horizontal arm 21 so as to guide the horizontal arm 21 in a vertical direction in slidable engagement with the slide rail 24a, and a stepping motor 25 serving as a part of an aspirating pipette ascending/descending drive source secured to the support plate 15.

Pulleys 26 and 27 are fixed to the upper end of the screw shaft 22 and an output shaft of the motor 25, respectively. A timing belt 28 is stretched across the pulleys 26 and 27. Therefore, the horizontal arm 21 can be vertically moved up and down according to the drive of the stepping motor 25.

To the right end of the horizontal arm 21 is fixed an aspirating pipette holding tool 16, which holds an aspirating pipette PT in a vertical direction in a replaceable (i.e., detachable) manner. The base end of the aspirating pipette PT is detachably connected to a flexible tube 17, and further, is connected to the sample aspirating pump 7 (see FIG. 1) via the flexible tube 17. Immediately under the aspirating pipette PT, a rack 14 is mounted on the base table 13. Into the rack 14 is inserted a sample container SP for containing a liquid sample (e.g., blood) therein. Here, the rack 14 and the sample container SP are inelastically supported by the base table 13 and the rack 14, respectively.

Moreover, to the support plate 15 is attached an aspirating pipette position detecting sensor 29 for detecting whether or not the horizontal arm 21 reaches an uppermost initial position.

The stepping motor 25 for ascending/descending the aspirating pipette is driven upon receipt of a drive pulse (i.e., a pulse current) as a motor driving current applied from a stepping motor drive circuit 9 (see FIG. 1) at each phase. Furthermore, in the case where rotating torque (i.e., drive force) need to be varied, a motor driving current (i.e., the magnitude of the drive pulse) is varied (or adjusted) by a motor current varying circuit (i.e., a drive force varying unit) 10 in accordance with an instruction issued from the controller 1.

As the motor drive circuit 9 is used a commercially available IC such as SLA7032M (manufactured by SANKEN ELECTRIC CO., LTD.); in the meantime, as the motor current varying circuit 10 is used a gate circuit for setting a drive current in the motor drive circuit 9.

The stepping motor 25 is driven by the drive pulse. The ascending/descending speed of the aspirating pipette PT depends upon the frequency of the drive pulse; in the meantime, an ascendent/descendent distance depends upon the total number of drive pulses to be supplied to the stepping motor 25. Additionally, the output torque (i.e., the drive force) of the motor is determined by the motor driving current (i.e., the magnitude of the drive pulse). The motor loses its synchronization at a load of the output torque or higher of the motor. The loss of synchronization signifies a state in which the rotation of the stepping motor cannot be synchronized with the supplied drive pulse.

The blood analyzer illustrated in FIG. 1 is designed to be operated in two modes: in an open mode (i.e., a first mode) and a closed mode (i.e., a second mode). Here, the open mode is a mode in which a container having an open upper portion (i.e., an open container) is used as the sample container SP; in contrast, the closed mode is a mode in which a container having an upper portion closed by a rubber cap or the like is used as the sample container SP.

Incidentally, the aspirating pipettes PT having tip ends different in shape are used in the open mode and in the closed mode.

Aspirating Pipette

Figure 3:
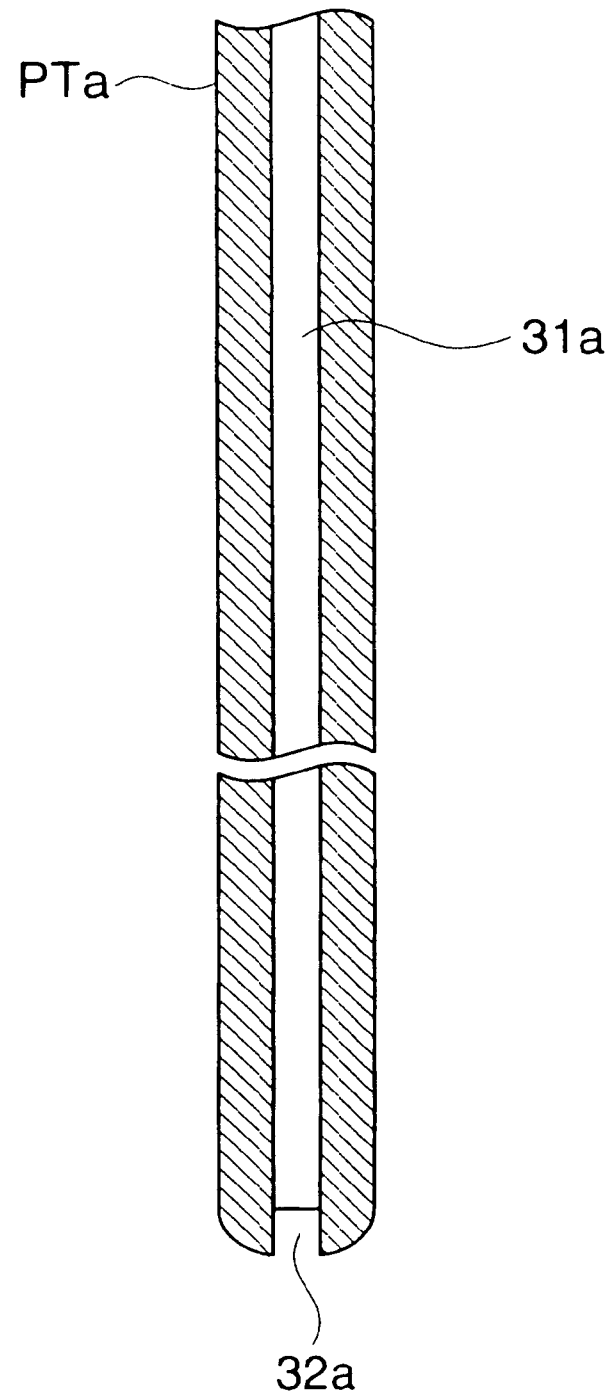
FIG. 3 is a cross-sectional view showing one example of an aspirating pipette shown in FIG. 2.
Figure 4:
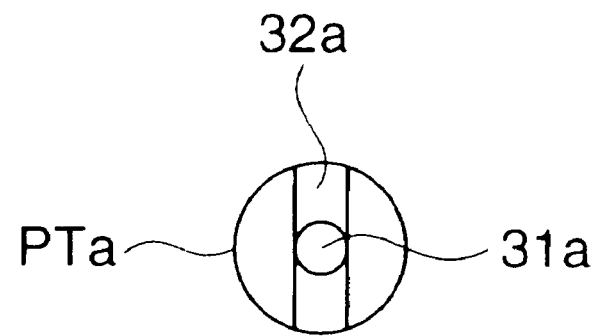
FIG. 4 is a front view showing one example of the aspirating pipette shown in FIG. 2.

FIG. 3 is a cross-sectional view showing an aspirating pipette PTa for use in the open mode, and FIG. 4 is a plan view showing the tip of the aspirating pipette PTa. The aspirating pipette PTa is preferably used for aspirating all of a sample from an open type sample container which contains a fine quantity of sample therein.

As shown in FIGS. 3 and 4, the aspirating pipette PTa is formed of a pipe made of stainless steel having an outer diameter of 1.5 mm, and includes a coaxial aspirating channel 31a having an inner diameter of 0.6 mm. The tip of the aspirating pipette PTa is flat and is rounded in a radius of 0.4 mm with a groove 32a cut transversely in a diametric direction. The groove 32a has the same width as the diameter of the aspirating channel 31a and a depth of 0.3 mm. Since the pipette PTa has the above-described shape of the tip, a sample staying in the vicinity of the bottom of the sample container SP is aspirated to the aspirating channel 31a through the groove 32a when an aspirating operation is performed with the tip brought into contact with the bottom of the sample container.

Figure 5:
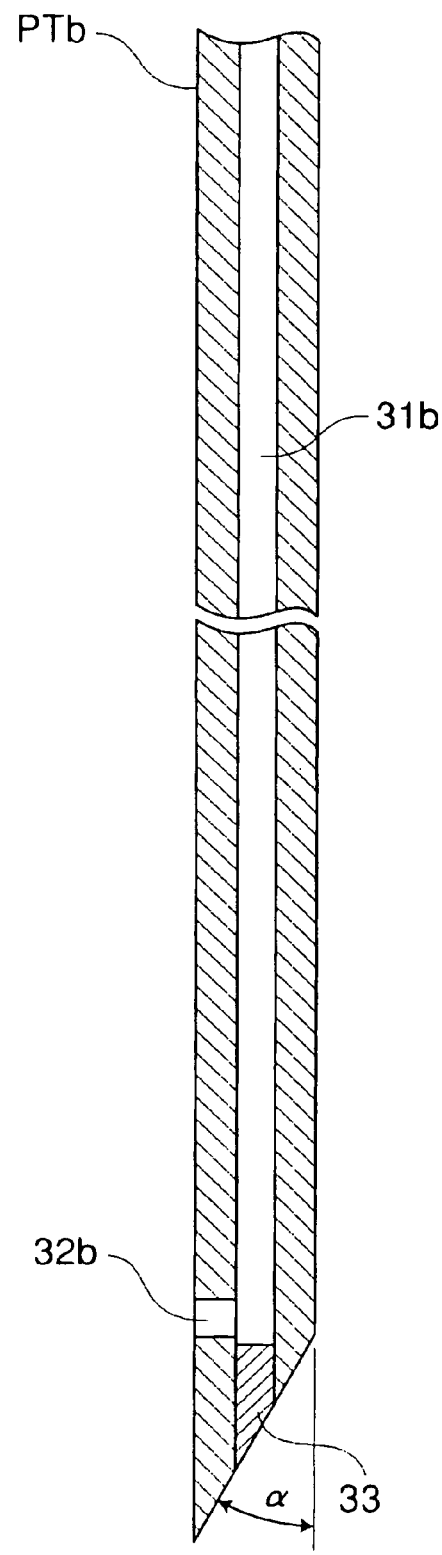
FIG. 5 is a cross-sectional view showing another example of the aspirating pipette shown in FIG. 2.

FIG. 5 is a longitudinally cross-sectional view showing an aspirating pipette PTb for use in the closed mode. The aspirating pipette PTb is formed of a pipe made of stainless steel having an outer diameter of 1.5 mm, and includes a coaxial aspirating channel 31b having an inner diameter of 0.6 mm. The tip is sharply cut at an angle α of 30° in such a manner as to readily break through a rubber cap when the sample container SP is the closed container with the rubber cap. The tip of the aspirating channel 31b is sealed with a sealing member 33 made of stainless steel, and further, an aspirating port 32b having an axis perpendicular to the axis of the pipette PTb is bored at its side surface.

Analyzing Operation

Figure 7:
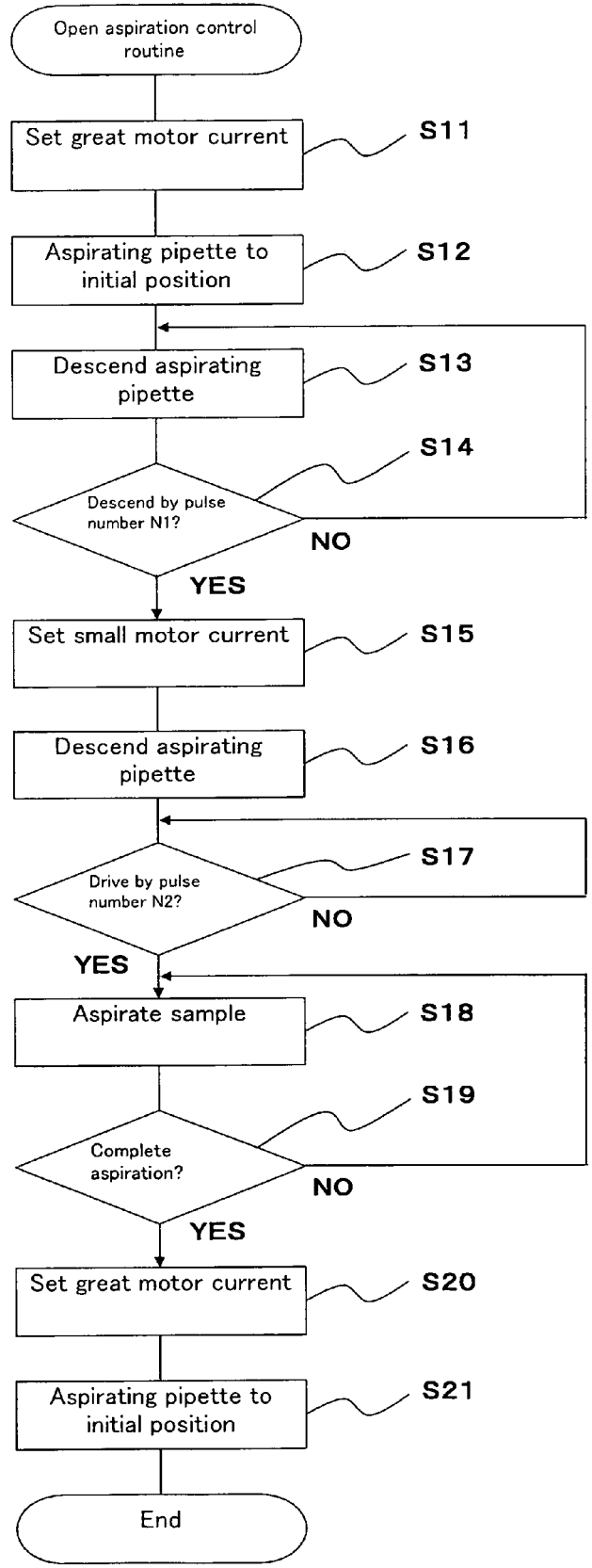
FIG. 7 is a flowchart illustrating the operation of the blood analyzer illustrated in FIG. 1.
Figure 8:
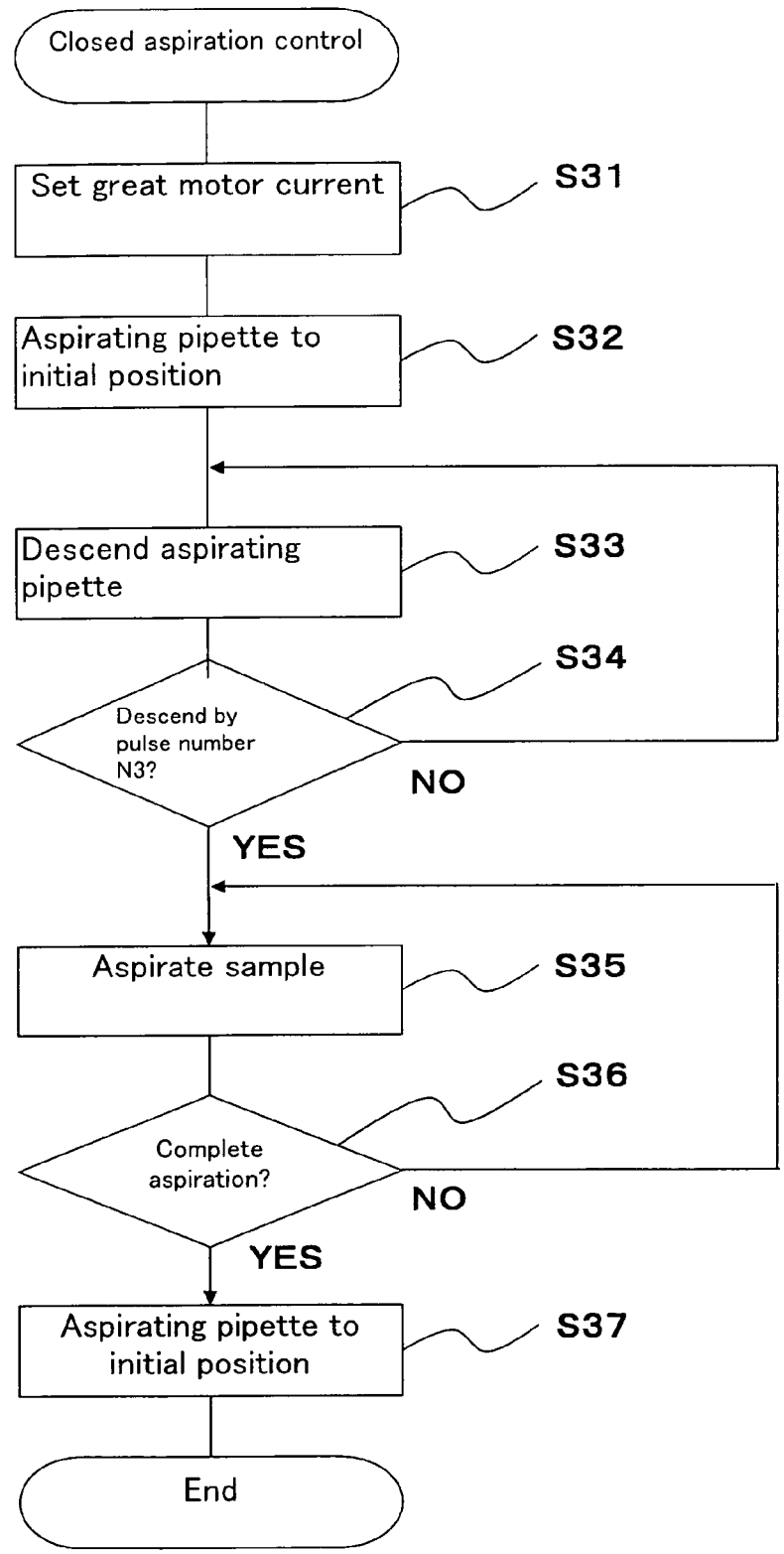
FIG. 8 is a flowchart illustrating the operation of the blood analyzer illustrated in FIG. 1.

Operations in the above-described configuration will be explained below in reference to flowcharts illustrated in FIGS. 6 to 8.

Figure 6:
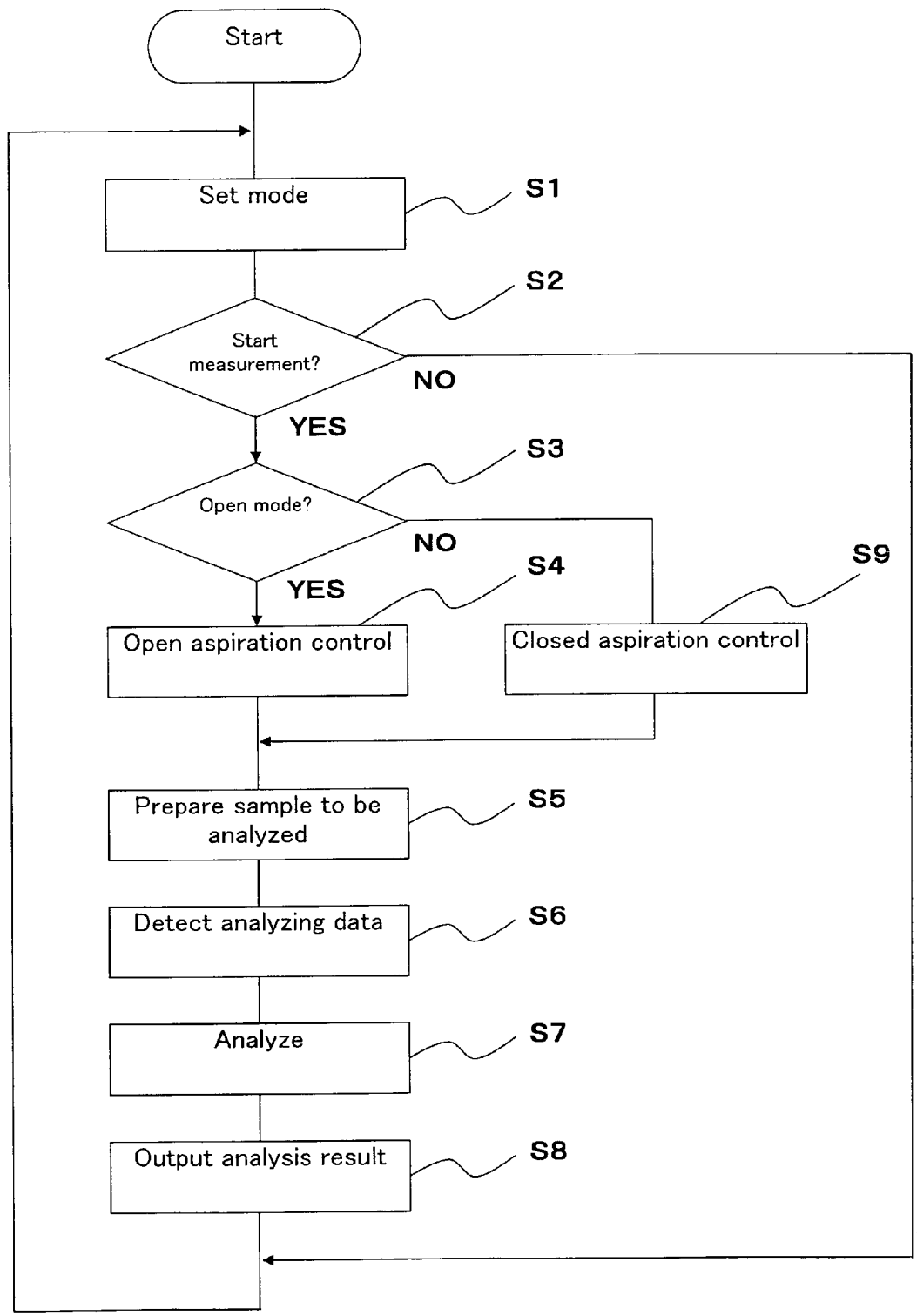
FIG. 6 is a flowchart illustrating operation of the blood analyzer illustrated in FIG. 1.

As illustrated in FIG. 6, first of all, a mode is set (step S1). That is to say, in the case where the sample container SP is the open container, the controller 1 executes the processing of setting "the open mode" when a user attaches the aspirating pipette PTa (see FIGS. 3 and 4) to the aspirating pipette holding tool 16 (see FIG. 2) and inputs "the open mode" in the touch panel 3 (see FIG. 1). In contrast, in the case where the sample container SP is the closed container, the controller 1 executes the processing of setting "the closed mode" when the user attaches the aspirating pipette PTb (see FIG. 5) to the aspirating pipette holding tool 16 and inputs "the closed mode" in the touch panel 3.

Subsequently, the controller 1 executes the processing of judging as to whether or not the user instructs measurement start (step S2).

Next, the setting mode is determined. If "the open mode" is set (step S3), the aspirating pipette ascender/descender 6 is driven by an open aspiration control, and then, the sample is aspirated from the sample container SP by the sample aspirating pump 7 (see FIG. 1) (step S4). A required reagent is added to the aspirated sample in the analyzing sample preparer 11, and thereby, the sample to be analyzed is prepared (step S5).

The electric and/or optical characteristics, that is, the analyzing data of the prepared sample to be analyzed is detected by the analyzing data detector 12 (step S6).

The controller 1 analyzes the sample based on the analyzing data, and then, the analysis result is displayed on the liquid crystal display 4 in the input/output unit 2 (steps S7 and S8).

Incidentally, if it is determined in step S3 that "the closed mode" is set, the control routine proceeds to step S9. The aspirating pipette ascender/descender 6 is driven by a closed aspiration control, and then, the sample is aspirated from the sample container SP by the sample aspirating pump 7. Thereafter, the control routine proceeds to step S5. The processing from steps S1 to S9 is repeated in sequence.

Open Aspiration Control

Subsequently, the processing procedures of "the open aspiration control" in step S4 will be explained below in reference to the flowchart illustrated in FIG. 7.

First of all, the controller 1 outputs a signal for setting the motor driving current (i.e., the magnitude of the drive pulse) to $I_1$. Upon receipt of the signal, the motor current varying circuit 10 sets the motor driving current in the motor drive circuit 9 to $I_1$ (step S1). Subsequently, the drive pulse is supplied to each of the phases of the stepping motor 25 from the motor drive circuit 9 at a predetermined frequency and the motor driving current $I_1$, thereby driving the stepping motor 25 in such a manner that the aspirating pipette PT is moved to an initial position.

When the sensor 29 (see FIG. 2) is actuated, that is, when the aspirating pipette PT reaches the initial position, the stepping motor 25 is stopped (step S12).

Thereafter, the stepping motor 25 is started to be driven in a direction in which the aspirating pipette PT is descended by the drive pulse of the motor driving current $I_1$ (step S13), and then, the stepping motor 25 is driven by the drive pulse whose pulse number $N_1(<N_0)$ has been programmed in advance (step S14). Here, $N_0$ designates the number of drive pulses of the stepping motor 25 corresponding to a distance from the tip of the aspirating pipette PT at the initial position to the bottom of the sample container SP. Consequently, at this time, the tip of the aspirating pipette PT has not reached the bottom of the sample container SP yet. At this moment, the motor current varying circuit 10 sets a motor driving current $I_2$, which has been programmed in advance, in the motor drive circuit 9 as a new motor driving current based on the output from the controller 1. In this case, the motor driving current $I_2$ is smaller than the motor driving current $I_1$ (step S15) Next, the stepping motor 25 is started to be driven by the drive pulse of the motor driving current $I_2$ in a direction in which the aspirating pipette PT is descended (step S16).

Subsequently, at the time when the stepping motor 25 is driven by the drive pulse whose pulse number $N_2(>N_1-N_1)$ has been programmed in advance, the energization to the stepping motor 25 is stopped (step S17). At this time, since $N_1+N_2>N_0$, the tip of the aspirating pipette PT reaches the bottom of the sample container SP, and thereafter, the drive pulse whose pulse number is $(N_1+N_2-N_0)$ is supplied to the stepping motor 25, thereby causing the loss of synchronization of the stepping motor 25 by reactive force exerted from the sample container SP on the aspirating pipette PT. This loss of synchronization lets the aspirating pipette PT inelastically press the bottom of the sample container SP for a predetermined period of time. Therefore, the tip of the aspirating pipette PT is satisfactorily pressed against the bottom of the sample container SP, thereby enabling a fine quantity of sample to be aspirated from the vicinity of the bottom of the sample container SP.

Incidentally, since the motor driving current of the stepping motor 25 during the loss of synchronization is $I_2$, which is set sufficiently smaller than $I_1$, the output torque of the stepping motor 25 is small, and therefore, there occurs no damage on the aspirating pipette PT, the sample container SP or the stepping motor 25.

Additionally, since the aspirating pipette PT is first descended at the motor driving current $I_1$ having the predetermined magnitude or greater, the synchronization of the stepping motor 25 is never lost during the execution in step S13.

Thereafter, the sample is aspirated from the sample container SP via the aspirating pipette PT by the sample aspirating pump 7 (step S18). When a predetermined quantity of sample is aspirated (step S19), the motor driving current of the stepping motor 25 is returned to $I_1$ (step S20). Subsequently, the stepping motor 25 is driven at the drive pulse of the motor driving current $I_1$, so that the aspirating pipette PT is ascended up to the initial position, that is, until the sensor 29 is actuated (step S21).

Closed Aspiration Control

Subsequently, the processing procedures of "the closed aspiration control" in step S9 will be explained below in reference to the flowchart illustrated in FIG. 8.

First of all, the controller 1 outputs the signal for setting the motor driving current to $I_1$. Upon receipt of the signal, the motor current varying circuit 10 sets the motor driving current in the motor drive circuit 9 to $I_1$ (step S31). Subsequently, the drive pulse is supplied to each of the phases of the stepping motor 25 from the motor drive circuit 9 at a predetermined frequency and the motor driving current $I_1$, thereby driving the stepping motor 25 in a direction in which the aspirating pipette PT is ascended or descended.

When the sensor 29 (see FIG. 2) is actuated, that is, when the aspirating pipette PT reaches the initial position, the stepping motor 25 is stopped (step S32). Here, the distance from the tip of the aspirating pipette PT at the initial position to the bottom of the sample container SP corresponds to the number $N_0$ of drive pulses of the stepping motor 25.

Thereafter, the stepping motor 25 is started to be driven in the direction in which the aspirating pipette PT is descended (step S33), and then, the stepping motor 25 is driven by the drive pulse whose pulse number $N_3(<N_0)$ has been programmed in advance (step S34).

Since $N_3<N_0$, the tip of the aspirating pipette PT stops at an appropriate position without any contact with the bottom of the sample container SP.

Thereafter, the sample is aspirated from the sample container SP via the aspirating pipette PT by the sample aspirating pump 7 (step S35). When a predetermined quantity of sample is aspirated (step S36), the stepping motor 25 is driven at the drive pulse of the motor driving current $I_1$, so that the aspirating pipette PT is ascended up to the initial position, that is, until the sensor 29 is actuated (step S37).

With the liquid aspirating pipette in the above-described preferred embodiment, in the open aspiration control, the tip of the aspirating pipette PT is securely pressed against the bottom of the liquid container SP by utilizing the loss of synchronization of the stepping motor 25, thereby securing the contact between the tip of the aspirating pipette PT and the liquid container SP with the remarkably simple configuration, so as to effectively aspirate a fine quantity of sample.

Incidentally, in the open aspiration control (see FIG. 7), the motor driving current may be set to $I_2$ before the start of the descending of the aspirating pipette, and further, the aspirating pipette may be brought into contact with the bottom of the sample container SP at the motor driving current $I_2$, thereby leading to the loss of the synchronization of the stepping motor.

Furthermore, although the same current $I_1$ has been used as the motor driving current in the open aspiration control and the motor driving current in the closed aspiration control in the above-described preferred embodiment, the present invention is not limited to this: for example, a current different from the current $I_1$ may be used as the motor driving current in the closed aspiration control. In this case, since the aspirating pipette PT need to penetrate the rubber cap of the sample container SP in the closed aspiration control, it is preferable that a current larger than the current $I_1$ should be used.

Additionally, although the stepping motor has been used as a part of the drive source in the above-described preferred embodiment, the present invention is not limited to this: for example, a fluid drive source such as an air motor or an air cylinder may be used as the drive source.

In addition, although the liquid aspirator 5 has been exemplified by the device for aspirating the blood from the sample container SP containing the blood therein in the above-described preferred embodiment, the liquid aspirator according to the present invention may be applied to a device for aspirating a liquid reagent from a reagent container containing the liquid reagent.

What is claimed is:

1. A liquid aspirator system for aspirating liquid from a liquid container for containing the liquid therein, the liquid aspirator comprising:
   an open container;
   an aspirating pipette;
   a stepping motor for descending the aspirating pipette into the open liquid container;
   a liquid aspirating pump for supplying pressure for aspirating liquid through the aspirating pipette;
   a position detecting sensor for detecting the positioning the pipette at an initial position;
   a drive circuit unit for supplying a motor drive current to the stepping motor; and
   a controller for controlling the stepping motor and the liquid aspirating pump;
   the controller controls the stepping motor with N number of drive pulses to output a predetermined drive force to move the pipette from the initial position, where the drive pulse number N has been programmed into the controller in advance, where a distance from a tip of the pipette to a bottom of the open liquid container corresponds to a number of drive pulses $N_0$ to a second position in contact with the bottom of the open liquid container ($N>N_0$), the movement of the pipette from the initial to the second position being effected and completed solely with supply of the N number of drive pulses to the stepping motor, wherein the controller controls the drive circuit unit to supply the motor drive current from the drive circuit unit to the stepping motor so as to descend the aspirating pipette and to continuously supply the motor drive current to the stepping motor after the aspirating pipette is brought into inelastic contact with the bottom of the open liquid container disposed under the aspirating pipette in the second position such that synchronization of the stepping motor is lost,
   wherein the controller controls the liquid aspirating pump so that the liquid aspirating pump aspirates the liquid through the aspirating pipette that contacts the bottom of the open liquid container in the second position.

2. The liquid aspirator system of claim 1, wherein the liquid aspirating pump supplies the pressure for aspirating the liquid contained in the open liquid container to the aspirating pipette in the second position.

3. The liquid aspirator system of claim 1, wherein the motor drive current comprises a pulse current of a predetermined frequency.

4. The liquid aspirator system of claim 1, wherein the controller controls the stepping motor in such a manner that the stepping motor outputs a second drive force when the aspirating pipette is descended from the initial position to a first position, the first position between the initial and second positions, the second drive force being larger than the predetermined drive force output when the aspirating pipette is descended from the first position to the second position at which the aspirating pipette is brought into contact with the bottom of the liquid container disposed under the aspirating pipette.

5. The liquid aspirator system of claim 4,
   wherein the controller varies the magnitude of the drive force by varying the magnitude of the motor drive current to be supplied to the stepping motor by the drive circuit unit.

6. The liquid aspirator system of claim 1, wherein the stepping motor comprises an output shaft rotated in synchronization with a pulse current.

* * * * *